US000001973H

(19) United States

(12) Statutory Invention Registration

Hu

(10) Reg. No.: US H1973 H

(43) Published: Jul. 3, 2001

(54) HUMAN NEUTROPHIL COLLAGENASE SPLICE VARIANT

(75) Inventor: Shou-Ih Hu, New Providence, NJ (US)

(73) Assignee: Novartis AG, Basel (CH)

(21) Appl. No.: 09/178,002

(22) Filed: Oct. 22, 1998

(51) Int. Cl.[7] ..... C12Q 1/68; G01N 33/53; C07H 21/04; C07K 16/00; A61K 39/00

(52) U.S. Cl. ..... 435/6; 435/69.3; 435/7.1; 536/23.5; 530/387.9; 424/185.1

(56) References Cited

PUBLICATIONS

Chubinskaya et al., Laboratory Investigation, vol. 74, No. 1, (1996).

Greenwald et al., Elsevier Science Inc., Bone, vol. 22, No. 1, pp. 33–38 (1998).

Hanemaaijert et al., The Journal of Biological Chemistry, vol. 272, No. 50, pp. 31504–31509(1997).

Shlopov et al., Arthritis & Rheumatism, vol. 40, No. 11, pp. 2065–2074 (1997).

*Primary Examiner*—Michael J. Carone
*Assistant Examiner*—Aileen J. Baker
(74) *Attorney, Agent, or Firm*—Gregory D. Ferraro

(57) ABSTRACT

The subject invention is related to human MMP-8alt genes and gene products and their differential expression when comparing a patient with a disease state to a control. A further aspect of the invention concerns compounds which antagonize the biological activity of MMP-8alt protein and methods for identifying these compounds. Another aspect of the present invention concerns pharmaceutical compositions comprising such compounds for the treatment of arthritis, cancer, and disease caused by cellular apoptosis including but not limited to Parkinson's disease, Alzheimer's disease and Huntington's chorea.

31 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

```
GCTCGCCAGGGAAGGGCCCTACCCAGAGGACAGAAAGAAAGCCAGGAGGG     50

GTAGAGTTTGAAGAGAAGATCATGTTCTCCCTGAAGACGCTTCCATTTCT    100
                        M  F  S  L  K  T  L  P  F  L
GCTCTTACTCCATGTGCAGATTTCCAAGGCCTTTCCTGTATCTTCTAAAG    150
 L  L  L  H  V  Q  I  S  K  A  F  P  V  S  S  K
AGAAAAATACAAAAACTGTTCAG GACTACCTGGAAAAGTTCTACCAATTA   200
E  K  N  T  K  T  V  Q | D  Y  L  E  K  F  Y  Q  L
```

```
CAGAATAAATAAGCCTTTTCTACAGTAGTGAAGAGGATAAAAAAGAGGAA
 Q  N  K  *
  R  I  N  K  P  F  L  Q  *  *  R  G  *  K  R  G
CTGCACTGATGCAACAAATACCTCAAGAGAAGTCAATTAAT

T  A  L  M  Q  Q  I  P  Q  E  K  S  I  N
```

```
CCAAGCAACCAGTATCAGTCTACAAGGAAGAATGGCACTAATGTGATCGT    250
 P  S  N  Q  Y  Q  S  T  R  K  N  G  T  N  V  I  V
```

FIG.2A

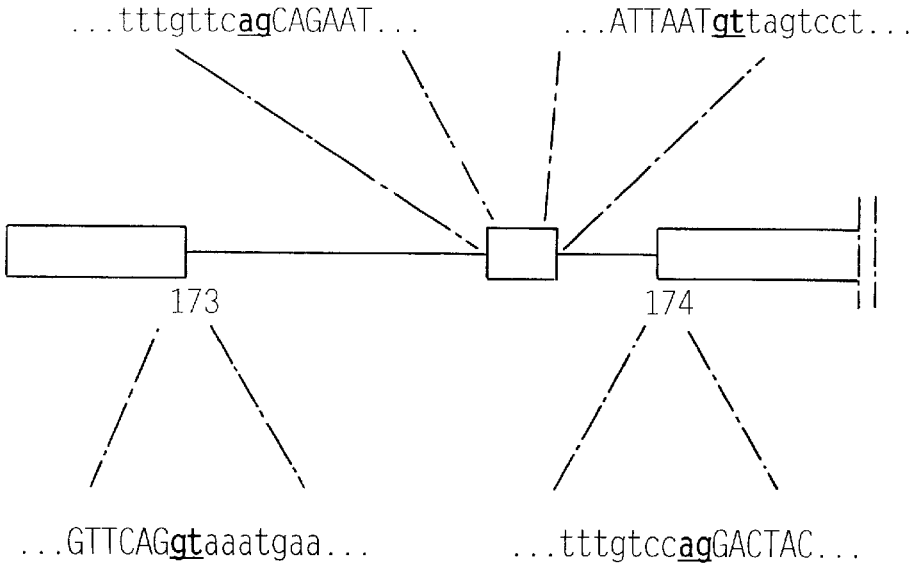

FIG.2B

HUMAN NEUTROPHIL COLLAGENASE SPLICE VARIANT

BACKGROUND

The interactions of cells with the extracellular matrix (ECM) are critical for the normal development and function of the organism. Modulation of cell-matrix interactions occurs through the action of unique proteolytic systems responsible for hydrolysis of a variety of ECM components. By regulating the integrity and composition of the ECM structure, these enzyme systems play a pivotal role in the control of signals elicited by matrix molecules, which regulate cell proliferation, differentiation, and cell death. The turnover and remodeling of ECM must be highly regulated since uncontrolled proteolysis contributes to abnormal development and to the generation of many pathological conditions characterized by either excessive degradation or a lack of degradation of ECM components.

Matrix metalloproteinases (MMPs) are a major group of enzymes that regulate cell-matrix composition. The MMPs are zinc-dependent endopeptidases known for their ability to cleave one or several ECM constituents as well as nonmatrix proteins. They comprise a large family of proteases that share common structural and functional elements and are products of different genes. Ample evidence exists on the role of MMPs in normal and pathological processes, including embryogenesis, wound healing, inflammation, arthritis, apoptosis and cancer. The association of MMPs with cancer metastasis has raised considerable interest because they represent an attractive target for development of novel antimetastatic drugs aimed at inhibiting MMP activity. Therefore, understanding the structure and function of these key enzymes has significant implications for cancer therapy. Massova, I., et al., (1998) The FASEB Journal, 12:1075–1095.

Most members of the MMP family are organized into three basic, distinctive, and well-conserved domains based on structural considerations: an amino-terminal propeptide; a catalytic domain; and a hemopexin-like domain at the carboxy-terminal. The propeptide consists of approximately 80–90 amino acids containing a cysteine residue, which interacts with the catalytic zinc atom via its side chain thiol group. A highly conserved sequence (. . . PGCGXPD . . . ) is present in the propeptide. Removal of the propeptide by proteolysis results in zymogen activation, as all members of the MMP family are produced in a latent form. The catalytic domain contains two zinc ions and at least one calcium ion coordinated to various residues. One of the two zinc ions is present in the active site and is involved in the catalytic processes of the MMPs. The second zinc ion (also known as structural zinc) and the calcium ion are present in the catalytic domain approximately 12 Å away from the catalytic zinc. The catalytic zinc ion is essential for the proteolytic activity of MMPs; the three histidine residues that coordinate with the catalytic zinc are conserved among all the MMPs. Little is known about the roles of the second zinc ion and the calcium ion within the catalytic domain, but the MMPs are shown to possess high affinities for structural zinc and calcium ions. Bode, W., et al., (1994) EMBO Journal, 13:1263–1269; Salowe S. P., et al., (1992) Biochemistry 31:4535–4540. The hemopexin-like domain of MMPs is highly conserved and shows sequence similarity to the plasma protein, hemopexin. The hemopexin-like domain has been shown to play a functional role in substrate binding and/or in interactions with the tissue inhibitors of metalloproteinases (TIMPs), a family of specific MMP protein inhibitors. Borden, P., and Heller R. A. (1997) Crit. Rev. Eukaryot. Gen. Expression 7:159–178; Gomis-Ruth, F. X., et al., Nature (London) 389:77–81. In addition to these basic domains, the family of MMPs evolved into different subgroups by incorporating and/or deleting structural and functional domains.

Neutrophil collagenase (MMP-8) is a member of the matrix metalloproteinase (MMP) family. It is capable of cleaving all three α-chains of types I, II, and III collagen. It is a secreted glycoprotein which is synthesized as a latent enzyme. The nucleotide sequence of MMP-8 cDNA (GenBank Accession No. J05556) encodes a protein of 467 amino acids, with a secretory signal sequence of 20 residues followed by the prodomain of 80 residues. The activation of this enzyme requires autolytic removal of 80 amino acids from the N-terminus. Devarajan, P., et al., (1991) Blood 77, 2731–2738; Hasty, K.A., et al., (1990) J. Biol. Chem. 265, 11421–11424. MMP-8 was previously thought to be expressed exclusively by neutrophils, but recently its expression has also been detected in chondrocytes and was found to be capable of cleaving aggrecan in cartilage. Amer, E.C., et al., (1997) J. Biol. Chem. 272, 9294–9299; Cole, A.A. et al. (1996) J. Biol. Chem. 271, 11023–11026; and Cole, A.A. and Kuettner, K.E. (1995) Acta Orthop. Scand. Suppl. 266, 98–102.

Recent studies have shown that MMP-8 is not a unique gene product of neutrophils since it is also expressed by chondrocytes in human articular cartilage Cole, A.A. et al. (1996) J. Biol. Chem. 271, 11023–11026; and Cole, A.A. and Kuettner, K.E. (1995) Acta Orthop. Scand. Suppl. 266, 98–102. It is capable of cleaving not only collagen but also aggrecan. Further, MMP-8 mRNA expression has been observed in mononuclear fibroblast-like cells in the rheumatoid synovial membrane and Western blot analysis shows a similar up-regulation at the protein level in arthritic conditions. Hanemaaijer R., et al., (1997) J. Biol. Chem. 12:272(50):31504-9. Accordingly, MMP-8 is involved in the causation of arthritis.

Pre-mRNA splicing is a widely used biological mechanism in higher eukaryotes for generating mature mRNA. More recently, it has become apparent that pre-mRNAs of many genes are capable of undergoing alternative splicing and generate multiple species of mature mRNA. Some of the splice variants occur at the non-coding region of the mRNA and do not influence the amino acid sequence of the translation products but may somehow affect translation efficiency. Rescheleit, D.K., et al., (1996) FEBS Letters 394, 345–348. On the other hand, alternative splicing can also occur at the coding region of the mRNA, resulting in translation products with different tissue distribution or subcellular localization. Kato, A., et al., (1997) J. Biol. Chem. 272, 15313–15322; Joun, H., et al., (1997) Endocrinology 138, 1742–1749; and Nilsen, H., et al., (1997) Nucleic Acids Res. 25, 750–755. The ability to detect such splicing variants for a given mRNA has greatly increased due to the use of polymerase chain reaction (PCR) coupled with the reverse transcription (RT) of mRNA.

Several members of MMP family whose genomic structure have been analyzed all contain an intron at the similar position as MMP-8. Collier, I.E., et al., (1988) J. Biol. Chem. 263, 10711–10713; Anglard, P., et al., (1995) J. Biol. Chem. 270, 20337–20344; and Pendas, A.M., et al., (1997) Genomics 40, 222–233. These include both collagenase-1 (MMP-1) and collagenase-3 (MMP-13). In the case of membrane-type MMPs, an extended family of MMP, an alternatively spliced MT-MMP-3 was identified recently. Matsumoto, S., et al. (1997) Biochim Biophys Acta 1354, 159–170. This alternative splicing occurs near the transmembrane region of MT-MMP-3, which results in soluble instead of membrane-anchored MT-MMP-3. RT-PCR has made it possible to identify alternative spliced form of MMPs.

In addition to extracellular matrix, the cytoskeleton proteins inside of cells are also essential for cellular functions such as vesicle movement inside of cells, cell division and migration, and even cell survival. Consequently, excess degradation of cytoskeleton proteins may also lead to arthritis, cancer, and disease caused by cellular apoptosis including but not limited to Parkinson's disease, Alzheimer's disease and Huntington's chorea. Therefore, there is a need for a process to diagnose the onset and progression of cytoskeleton protein degradation in order to assess appropriate therapeutic measures and their effectiveness.

There is also a need to detect and measure the differential expression of genes and gene products which are altered in this disease state, such that this differential expression can be determined diagnostically to predict the onset of the disease state.

A further need exists for identifying additional factor(s) and others which interact with and regulate the biological function of the gene and gene products which show differential expression in cytoskeleton protein degradation, so that they may be administered to patients in need of such treatment.

There also exists a need for pharmaceuticals comprising the factor(s) which interact with the gene and gene products that are active in the above-described disease states and/or are differentially expressed in these disease states such that they may be administered to a patient in need thereof for the treatment and/or prevention of these disease states.

SUMMARY

The nucleotide sequence of the gene described herein is a splice variant of the nucleotide sequence of human neutrophil collagenase (MMP-8) (SEQ ID NO:3) and has a 91 base pair insertion between codons for amino acid residues 34 and 35 of MMP-8 cDNA (SEQ ID NO:3). This splice variant encodes an open reading frame for a 444-residue protein (SEQ ID NO:2) which lacks a secretory signal sequence. Therefore, as opposed to MMP-8, the translation product of MMP-8alt is not a secreted protein, however, it is enzymatically active. Accordingly, the nucleotide sequences and polypeptides encoded thereby of the present invention are referred to herein as "MMP-8alt", "MMP-8alt cDNA", "MMP-8alt mRNA", "human MMP-8alt", "MMP-8alt protein" and "MMP-8alt polypeptide".

Toward these ends, and others, it is an aspect of the invention to provide polynucleotides that encode MMP-8alt protein. In a preferred embodiment of this aspect of the invention the polynucleotide comprises the region encoding human MMP-8alt in the sequence set out in SEQ ID NO:1. In accordance with this aspect of the invention there are provided isolated nucleic acid molecules encoding human MMP-8alt including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives. Among the particularly preferred embodiments of this aspect of the invention are naturally occurring allelic variants of human MMP-8alt.

It also is an object of the invention to provide human MMP-8alt polypeptides, particularly human MMP-8aft polypeptides, that are differentially expressed in diseased conditions and therefore, when detected via assay, allows a diagnosis of diseased conditions. In a preferred embodiment the polypeptide comprises the sequence shown in SEQ ID NO:2. In accordance with this aspect of the invention there are provided polypeptides of human origin as well as biologically, diagnostically or therapeutically useful fragments, variants and derivatives thereof, variants and derivatives of the fragments, and analogs of the foregoing.

It is another object of the invention to provide a process for producing the aforementioned polypeptides, polypeptide fragments, variants and derivatives, fragments of the variants and derivatives, and analogs of the foregoing. In a preferred embodiment of this aspect of the invention there are provided methods for producing the aforementioned human MMP-8alt polypeptides comprising culturing host cells having expressibly incorporated therein a vector containing an exogenously-derived human MMP-8alt-encoding polynucleotide under conditions for expression of human MMP-8alt polypeptides in the host and then recovering the expressed polypeptide.

In accordance with yet another aspect of the present invention, there are provided human MMP-8alt antagonists (inhibitors) and methods for identifying such antagonists, wherein such antagonists reduce or prevent the effect of human MMP-8alt polypeptide. Among preferred antagonists are those which mimic human MMP-8alt so as to bind to human MMP-8alt receptor or binding molecules but do not elicit a human MMP-8alt-induced response or more than one human MMP-8alt-induced response. In another embodiment of this aspect of the present invention there are provided antagonists which are small molecules and antibodies and the like which bind to human MMP-8alt polypeptide and regulate its biological activity. Also among preferred antagonists are molecules that bind to or interact with human MMP-8alt so as to inhibit an effect of human MMP-8alt or more than one effect of human MMP-8alt or which prevent expression of human MMP-8alt polynucleotide transcript. In accordance with this aspect of the invention there are provided assays for detecting antagonists to human MMP-8alt which regulate human MMP-8alt expression and/or activity. In accordance with one embodiment of this aspect of the invention there is provided anti-sense polynucleopides which regulate transcription of the human MMP-8alt gene.

Another aspect of the present invention encompasses assay techniques for detecting disease conditions associated with MMP-8alt expression by measuring human MMP-8alt expression levels in bodily samples, preferably body tissue and fluid samples. A preferred embodiment of the assay aspect of the invention provides assays for measuring human MMP-8alt mRNA expression in body tissue samples derived from a patient. Another embodiment of the assay aspect of the invention provides assays for measuring human MMP-8alt polypeptide levels comprising incubating a body tissue or fluid sample, which has been obtained from a patient, with an anti-human MMP-8alt antibody and measuring the level of bound anti-human MMP-8alt antibody in the body tissue or fluid sample.

In certain additional preferred embodiments of this aspect of the invention there -are provided antibodies against human MMP-8aft polypeptides and methods for their production. In certain particularly preferred embodiments in this regard, the antibodies are highly selective for human MMP-8alt polypeptides or portions of human MMP-8alt polypeptides.

In still another embodiment of the present invention there are provided methods of treating conditions resulting from expression of human MMP-8alt comprising administering antagonists to human MMP-8alt in pharmaceutically acceptable amounts to treat conditions resulting from the activity of human MMP-8alt.

In yet another aspect of the present invention there are provided kits comprising the components necessary for detecting an above-normal expression of human MMP-8alt polynucleotides or polypeptides in body tissue samples derived from a patient.

In accordance with another object the invention there are provided products, compositions, processes and methods that utilize the aforementioned polypeptides and polynucleotides for research, biological, clinical and-therapeutic purposes, inter alia.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 2. Nucleotide sequence and genomic structure of MMP-8 around the 91 bp insert. (A) nucleotide sequence of the 5' 250 bp of MMP-8 cDNA and the sequence of the 91 bp insert. The nucleotide sequence of the 91 bp inset is shown in the box. Numeration follows the published sequence. The putative new methionine initiation codon for MMP-8alt is underlined and in boldface. (B) Genomic organization of MMP-8 gene encodes two alternatively spliced transcripts. Drawing shows splicing patterns that generate MMP-8 and MMP-8alt transcripts. Open boxes represent exons, and lines represent introns. Numbers indicate the positions in the MMP-8 cDNA. Consensus splice donor/acceptor sites are underlined and in boldface.

DEFINITIONS

Figure 1:
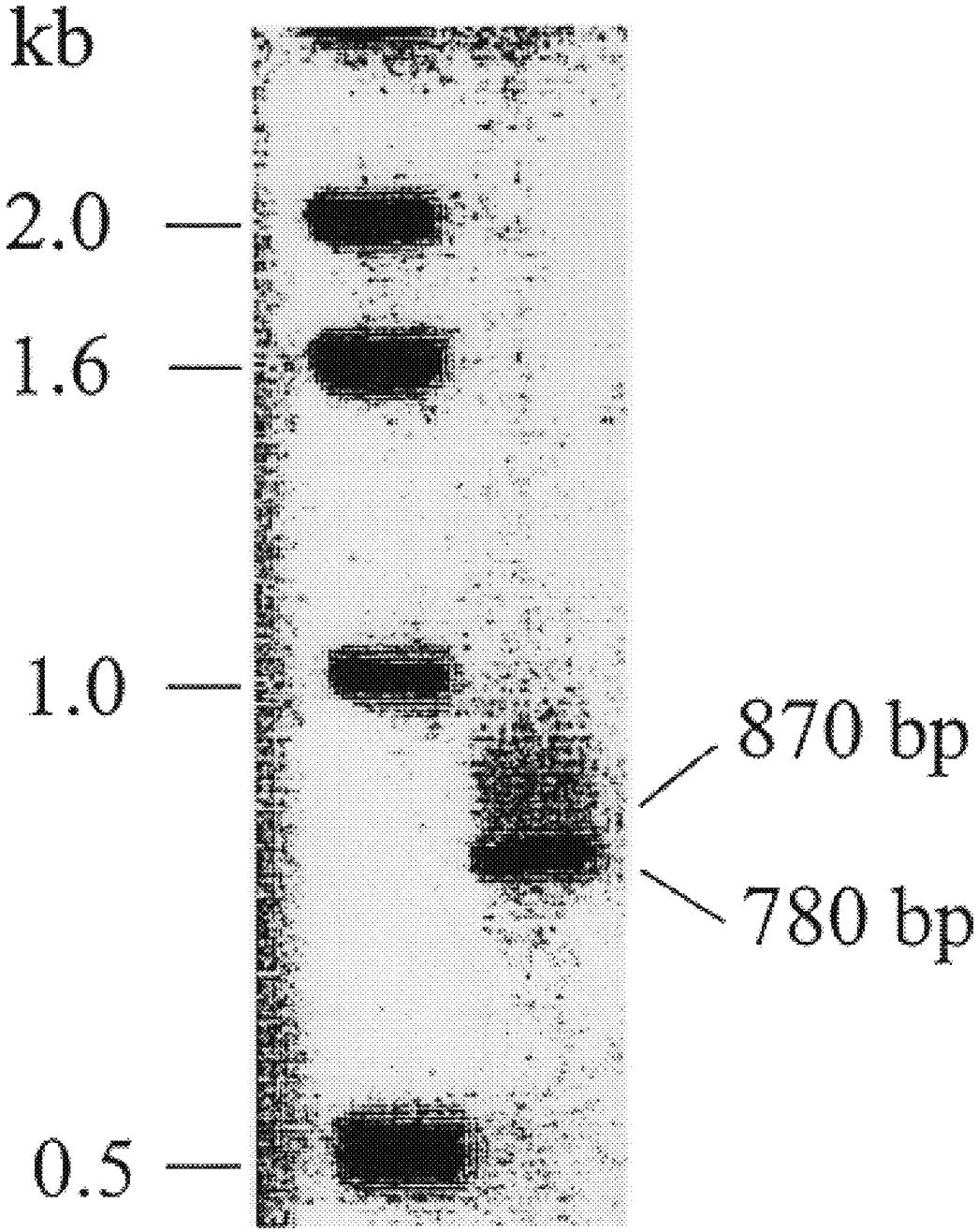
FIG. 1. Analysis of the RT-PCR products generated from U937 cells using primer pair A/B. Primer A corresponds to nucleotides 68 to 77 of MMP-8 cDNA in the sense orientation, and primer B corresponds to nucleotides 827 to 850 of MMP-8 cDNA in the antisense orientation. The RT-PCR condition is described in example 1. The two bands generated are ~780 base pair (bp) and ~870 bp, respectively.

The following illustrative explanations are provided to facilitate understanding of certain terms used frequently herein, particularly in the examples. The explanations are provided as a convenience and are not limitative of the invention.

"Identity" as the term is used herein, refers to a polynucleotide or polypeptide sequence which comprises a percentage of the same bases as a reference polynucleotide or polypeptide (SEQ ID NO:1 or SEQ ID NO:2). For example, a polynucleotide or polypeptide which is at least 90% identical to a reference polynucleotide or polypeptide, has polynucleotide bases or amino acid residues which are identical in 90% of the bases or residues which make up the reference polynucleotide or polypeptide and may have different bases or residues in 10% of the bases or residues which comprise that polynucleouide or polypeptide sequence. Exemplary algorithms for determining "identity" are the BLAST program (Basic Local Alignment Search Tool at the National Center for Biological Information (Altschul S. F. et al., J. Mol. Biol. (1990) 215(3):403–410) and FAST program. "Identity" may be determined by procedures which are well-known in the art.

The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

"Recombinant" proteins refer to proteins produced by recombinant DNA techniques; i.e., produced from cells transformed by an exogenous DNA construct encoding the desired proteins. "Synthetic" polypeptides are those prepared by chemical synthesis.

A DNA "coding sequence of" or a "nucleotide sequence encoding" a particular protein, is a DNA sequence which is transcribed and translated into a protein when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

"Plasmids" generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

"Digestion of DNA" refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 $\mu$g of plasmid or DNA fragment is digested with about 2 units of enzyme in about 20 $\mu$l of reaction buffer. For the purpose of isolating DNA fragments for plasmid construction, typically 5 to 50 $\mu$g of DNA are digested with 20 to 250 units of enzyme in proportionately larger volumes.

"Genetic element" generally means a polynucleotide comprising a region that encodes a polypeptide or a region that regulates transcription or translation or other processes important to expression of the polypeptide in a host cell, or a polynucleotide comprising both a region that encodes a polypeptide and a region operably linked thereto that regulates expression.

"Ligation" refers to the process of forming phosphodiester bonds between two or more polynucleofides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. (1989) and Maniatis et al., pg. 146, as cited below.

"Oligonucleotide(s)" refers to relatively short polynucleotides. Often the term refers to single-stranded deoxyribonucleotides, but it can refer as well to single-or double-stranded ribonucleotides, RNA:DNA hybrids and double-stranded DNAs, among others.

"Polynucleotide(s)" generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single-and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

"Polypeptides", as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS - STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York (1983); Seifter et al., Analysis for protein modifications and nonprotein cofactors, Meth. Enzymol. 182: 626–646 (1990) and Rattan et al., Protein Synthesis: Posttranslational Modifications and Aging, Ann. N.Y. Acad. Sci. 663: 48–62 (1992).

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cell often carry out the same posttranslational glycosylations as mammalian cells and, for this reason, insect cell expression systems have been developed to express efficiently mammalian proteins having native patterns of glycosylation, inter alia. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell. The term "polypeptide" is used interchangeably herein with the terms "compound(s)", "polypeptides" and "protein(s)".

"Variant(s)" of polynucleotides or polypeptides, as the term is used herein, are polynucleotides or polypeptides that differ from a reference polynucleotide or polypeptide, respectively. Variants in this sense are described below and elsewhere in the present disclosure in greater detail.

(1) A polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino add substitutions, additions, deletions, fusions and truncations in the polypeptide encoded by the reference sequence, as discussed below.

(2) A polypeptide that differs in amino acid sequence from another, reference polypeptide. Generally, differences are limited so that the sequences of the reference and the variant are closely similar overall and, in many region, identical.

A variant and reference polypeptide may differ in amino acid sequence by one or more substitutions, additions, deletions, fusions and truncations, which may be present in any combination.

DESCRIPTION

Human MMP-8alt Polynucleotides and Polypeptides

Two distinct DNA fragments from human U937 cells were identified by RT-PCR using primers A and B (SEQ ID NOS:5 and 6, see Example 1). The sizes of these two fragments are ~780 bp and ~870 bp, respectively as shown in FIG. 1. These two PCR products were recovered and sequenced. The ~780 bp fragment matches exactly to the corresponding MMP-8 cDNA sequence in GenBank, whereas the ~870 bp fragment contains an additional 91 bp between residues 173 and 174 of the published sequence, as shown in FIG. 2A. This additional segment of the transcript is the result of an alternative splicing of the MMP-8 pre-mRNA.

Primers C and D (SEQ ID NOS:7 and 8, see Example 1) were utilized to amplify the genomic DNA To identify the potential intronic sequence of the genomic DNA which corresponds to the cDNA insert of MMP-8. These two primers are located at the 5' side and the 3' side of the 91 bp insert, respectively. A 2.5 kb DNA fragment was generated from the reaction. This 2.5 kb fragment contains an intron about 2.3 kb in length which separates residues 173 and 174 of the cDNA sequence of SEQ ID NO:1. The 91 bp sequence (nucleotide 174 to 264 of SEQ ID NO:1) is within this intronic sequence. In addition, the 91 bp insert was immediately preceded by a consensus splice-acceptor sequence, AG, at the 5' junction and immediately followed by a consensus splice donor sequence, GT, at the 3' junction (FIG. 2B). Therefore, this shows that the 91 bp insertion is the result of alternative splicing of the pre-mRNA to include an additional exon. Mount S. M., (1982) Nucleic Acids Res. 10:459–472. The two introns 5' and 3' of this 91 bp alternative exon are 1.9 kb and 360 bp, respectively.

Figure 3A:
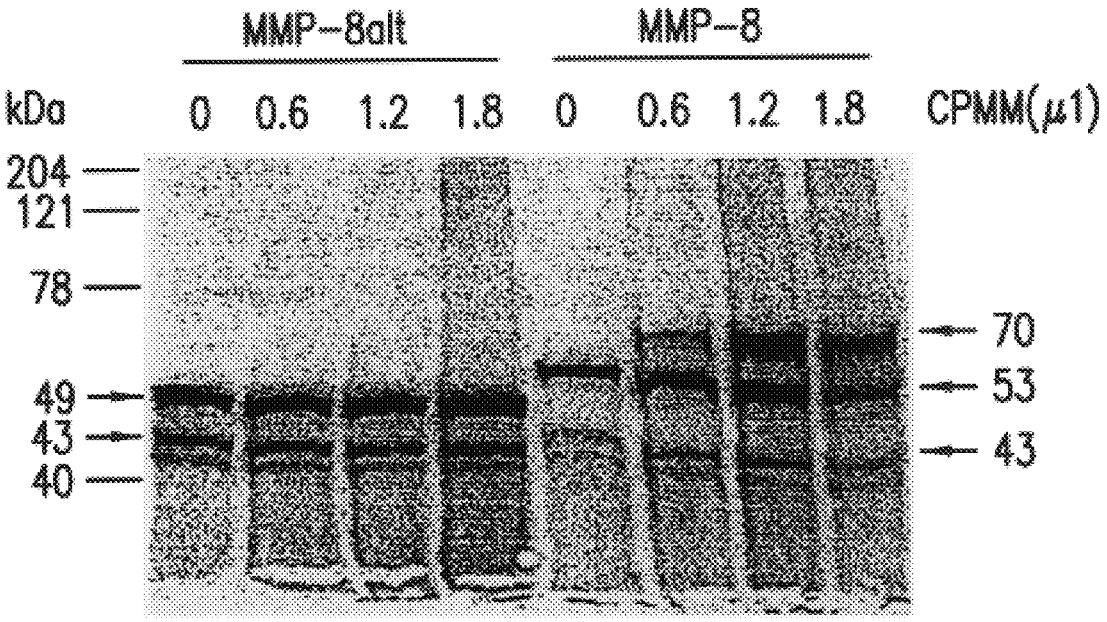
FIG. 3. Analysis of in vitro translated MMP-8 and MMP-8alt. (A) In vitro translation of MMP-8 and MMP-8alt were carried out in the absence or presence of indicated amounts of Canine Pancreatic Microsomal Membranes (CPMM). (B) In vitro translated MMP-8 and MMP-8alt were activated by treatment with p-aminophenylmercuric acetate (APMA). Lane 1, MMP-8; lane 2, MMP-8alt; lane 3, MMP-8+2 mM APMA; and Lane 4, MMP-8alt+2 mM APMA.

The 91 bp insert interrupts amino acid residues 34 and 35 in the prodomain of the MMP-8 protein (SEQ ID NO:4). All three possible reading frames of this insert contain stop codons. One of which has three stop codons followed by an ATG that is in frame with the rest of MMP-8 coding sequence. The next potential initiation codon is found at nucleotide 323, Met85 of MMP-8 (SEQ ID NO:4). cDNA encoding MMP-8 and MMP-8alt were subjected to in vitro transcription and translation. In vitro translated MMP-8 generated two major products of approximately 53 kDa and 43 kDa (FIG. 3A). In vitro translated MMP-8alt yielded two major products of approximately 49 kDa and 43 kDa (FIG. 3A). The 43 kDa product in both cases is a translation product starting at Met85 of MMP-8 and the corresponding methionine in MMP-8alt. The 49 kDa protein would be the result of translation from the new methionine within the 91 bp insert.

Figure 3B:
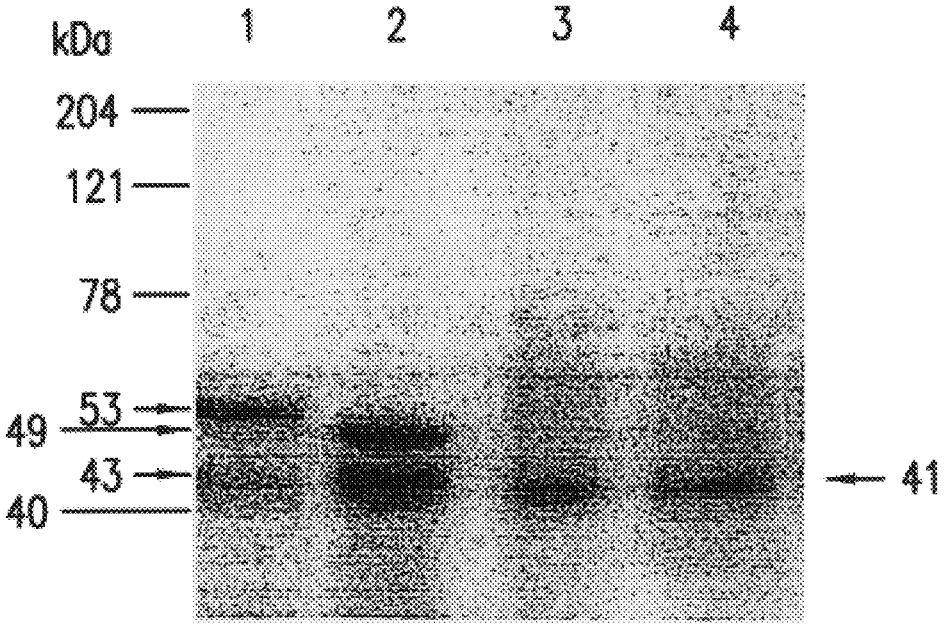

MMP-8alt is not processed for secretion in the same way as MMP-8. To verify this, the translation products were further analyzed for co-translational processing and core glycosylation by the addition of canine pancreatic microsomal membranes which generated higher molecular weight products. In vitro translation of MMP-8, but not MMP-8alt, in the presence of canine pancreatic microsomal membranes generated higher molecular weight products of 70 kDa in sizes (FIG. 3A). See Example 2. This result is in agreement with the fact that MMP-8 but not MMP-8alt possesses a signal sequence to translocate the protein into the microsomal membranes for glycosylation Activation of MMPs requires the removal of the prodomain from the protein by autolytic cleavage via a cysteine switch activation mechanism. Van Wart, H.E. and Birkedal-Hansen, H. (1990) Proc. Nati. Acad. Sci. 87, 5578–5582. This activation can also be achieved in a test tube by treatment of MMPs with p-aminophenylmercuric acetate, which stimulates autolysis. The critical cysteine residue of MMP-8 is cysteine 91. This cysteine residue is present in all three translation products mentioned above. Upon treatment with p-aminophenylmercuric acetate both in vitro translated MMP-8 and MMP-8alt are converted to a 41 kDa form (FIG. 3B). This size change is consistent with the size conversion of proenzyme to the active enzyme. The 43 kDa internal translation product, amino acids 85 to 467 of MMP-8 (SEQ ID NO:4), is also converted to the 41 kDa form (FIG. 3B).

The protein generated from MMP-8alt is enzymatically active since autoactivation experiments, see Example 2, shows that protein generated from the MMP-8alt transcript undergoes autolysis to generate a protein with a size consistent with the active form of MMP-8. Additionally, the alternatively spliced transcript of MMP-8, MMP-8alt, is also not unique to U937 cells. In addition, it is detected in human chondrocytes and THP-1 cells by RT-PCR.

In accordance with the above there are provided isolated polynucleotides that encode the MMP-8alt polypeptide having the deduced amino acid sequence of SEQ ID NO:2. Also among preferred embodiments of this aspect of the present invention are polynucleotides comprising fragments of MMP-8aft, most particularly fragments of the MMP-8alt having the polynucleotide sequence set out in SEQ ID NO:1, and fragments of variants and derivatives of the MMP-8alt of SEQ ID NO:1. In a most preferred embodiment the fragments will comprise the polynucleotide sequence encoding amino acid 77 to amino 238 of the amino acid sequence of SEQ ID NO:2.

In this regard a fragment is a polynucleotide having a nucleotide sequence that entirely is the same as part but not all of the nucleotide sequence of the aforementioned MMP-8alt polynucleotides and variants or derivatives thereof.

Using the information provided herein, such as the polynucleotide sequence set out in SEQ ID NO: 1, a polynucleotide of the present invention encoding a human MMP-8alt polypeptide may be obtained using standard cloning and screening procedures, such as those for cloning cDNAs using mRNA from cells of human tissue as starting material. The cDNA sequence contains an open reading frame encoding a protein of about 444 amino acid residues with a deduced molecular weight of about 49 kDa. The protein exhibits greatest homology to MMP-8.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in SEQ ID NO:1. It also may be a polynucleotide with a different sequence, which, as a result of the redundancy (degeneracy) of the genetic code, encodes the polypeptide of SEQ ID NO:2.

Polynucleotides of the present invention which encode the polypeptide of SEQ ID NO:2 may include, but are not limited to the coding sequence for the mature polypeptide, by itself; the coding sequence for the mature polypeptide and additional coding sequences, such as a pre, or pro- or prepro- protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example, ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide.

The present invention further relates to variants of the hereinabove described polynucleotides which encode for fragments, analogs and derivatives of the polypeptide having the deduced amino acid sequence of SEQ ID NO:2. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Further particularly preferred in this regard are polynucleotides encoding MMP-8alt variants, analogs, derivatives and fragments, and variants, analogs and derivatives of the fragments, which have the amino acid sequence of the MMP-8alt polypeptide of SEQ ID NO:2 in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of MMP-8alt. Also especially preferred in this regard are conservative substitutions. Highly preferred are polynucleotides encoding polypeptides having the amino acid sequence of SEQ ID NO:2 without substitutions. Most highly preferred are variants of MMP-8alt polypeptide which comprise amino acid 77 to amino acid 238 of SEQ ID NO:2.

Further preferred embodiments of the invention are polynucleotides that are at least 90% identical to a polynucleotide encoding the MMP-8alt polypeptide having the amino acid sequence set out in SEQ ID NO:2, and polynucleotides which are complementary to such polynucleofides. Alteratively, most highly preferred are polynucleotides that comprise a region that is at least 95% identical to a polynucleotide encoding the MMP-8alt polypeptide and polynucleotides complementary thereto. Furthermore, those with at least 97% are highly preferred among those with at least 95%, and among these those with at least 98% and at least 99% are particularly highly preferred, with at least 99% being the more preferred.

Particularly preferred embodiments in this respect, moreover, are polynucleotides which encode polypeptides which retain substantially the same biological function or activity as the polypeptide encoded by the cDNA of SEQ ID NO:2.

The present invention further relates to polynucleotides that hybridize to the herein above-described sequences under stringent conditions. As herein used, the term "stringent conditions" includes moderate or severe stringency. Conditions of moderate stringency, as defined by Sambrook et al. Molecular Cloning: A Laboratory manual, 2 ed. Vol. 1, pp. 101–104, Cold Spring Harbor Laboratory Press, (1989), include use of a prewashing solution of 5.X SSC, 0.5% SDS, 1.0 mM EDTA (pH 8.0) and hybridization condition of about 55° C., 5 X SSC, overnight. Conditions of severe stringency include higher temperatures of hybridization and washing. The skilled artisan will recognize that the temperature and wash solution salt concentration may be adjusted as necessary according to factors such as the length of the probe. In this regard, the present invention especially relates to polynucleotides which hybridize under stringent conditions to the herein above-described polynucleotides.

The polynucleotides and polypeptides of the present invention may be employed as research reagents and materials for discovery of treatments and diagnostics to human disease, as further discussed herein relating to polynucleotide assays, inter alia.

In sum, a polynucleotide of the present invention may encode a mature protein, a preprotein, a precursor of a mature protein having one or more prosequences which are not the leader sequences of a preprotein, or a preproprotein, which is a precursor to a proprotein, having one or more prosequences, which generally are removed during processing steps that produce active and mature forms of the polypeptide.

The polynucleotides described herein may be used as targets for identifying compounds which inhibit expression of MMP-8alt polynucleotides to prevent the expression and biological action of MMP-8alt protein.

Also with respect to this aspect of the present invention there is provided human MMP-8alt polypeptides, among other things, as described in greater detail below. Human MMP-8alt exhibits autocatalytic cleavage and endoproteolytic activity against intracellular cytoskeleton proteins. Accordingly, the MMP-8aft proteins of the present invention control vesicle movement inside of cells, cell division and migration, and cell survival. Accordingly, the inhibition of MMP-8alt protein may be employed to treat and/or prevent arthritis, cancer and cancer metastases; and diseases caused by cellular apoptosis including but not limited to Parkinson's disease, Alzheimer's disease and Huntington's chorea.

The MMP-8alt splice variant (SEQ ID NO:2) has a 91 bp insertion between residues 173 and 174 of MMP-8 (SEQ ID NO:4). This insertion is between amino acid residues 34 and 35 in the prodomain of MMP-8 (SEQ ID NO:4) and encodes an additional 11 amino acids as shown in FIG. 2A (SEQ ID NO:2) due to the internal methionine start codon. The MMP-8 alt splice variant encodes a 444 residue protein (SEQ ID NO:2) which lacks a secretory signal. Accordingly, MMP-8alt is not a secreted protein. However, as shown in example 2, the protein is enzymatically active. Within the 444 amino acid protein, the catalytic domain comprises amino acid 77 to 238 of SEQ ID NO:2; the cysteine-switch region comprises amino acid 66 to 74 of SEQ ID NO:2 and the putative zinc binding regions comprises amino 191 to 201 of SEQ ID NO:2. In short, the MMP-8alt protein lacks the initial 34 amino acids of the MMP-8 protein (SEQ ID NO:4) and contains an additional 11 amino acids in the insertion which MMP-8 lacks.

MMP-8alt polypeptides which have the deduced amino acid sequence of SEQ ID NO:2 are provided, as well as fragments, derivatives and analogs of such polypeptide. The terms "fragment," "derivative" and "analog" when referring to the polypeptide SEQ ID NO:2 means a polypeptide which retains essentially the same biological function or activity as such polypeptide by retaining the catalytic domain. Thus, an analog includes a proprotein which can be activated by cleavage of the proprotein portion to produce an active polypeptide. The polypeptide of the present invention may be a recombinant polypeptide, a natural polypeptide or a synthetic polypeptide, preferably a recombinant polypeptide.

The fragments, derivatives or analogs of the polypeptide of SEQ ID NO:2 may be (i) one in which one or more of the amino acid residues are substituted with a conserved or non-conserved amino acid residue (preferably a conserved amino acid residue) and such substituted amino add residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which the additional amino acids are fused to the polypeptide for purification of the polypeptide or a proprotein sequence. However, all fragments, derivatives or analogs of the polypeptide of SEQ ID NO:2 will comprise amino acid 77 to 238 of SEQ ID NO:2. Such fragments, derivatives and analogs are deemed to be within the scope of those skilled in the art from the teachings herein.

The polypeptides of the present invention include the polypeptide of SEQ ID NO:2 as well as polypeptides which have at least 90% similarity (preferably at least 90% identity) to the polypeptide of SEQ ID NO:2 and more preferably at least and more preferably at least 95% similarity (still more preferably at least 95% identity) and even more preferably at least 97% similarity (still more preferably at least 97% identity) and most preferably at least 99% similarity (still more preferably at least 99% identity) to the polypeptide of SEQ ID NO:2.

A variant, i.e. a "fragment", "analog" or "derivative" polypeptide, and reference polypeptide may differ in amino acid sequence by one or more substitutions, additions, deletions, fusions and truncations, which may be present in any combination. However, all variants of the amino acid sequence of SEQ ID NO:2 will contain the minimum catalytic domain which is a fragment containing amino acid 77 to amino acid 238 of SEQ ID NO:2.

Among preferred variants are those that vary from a reference by conservative amino acid substitutions. Such substitutions are those that substitute a given amino acid by another amino acid of like character. Conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gin, exchange of the basic residues Lys and Arg and replacements among the aromatic residues Phe, Tyr.

Also among preferred embodiments of this aspect of the present invention are polypeptides comprising fragments of MMP-8alt, most particularly fragments of the MMP-8alt having the amino acid set out in SEQ ID NO:2, and fragments of variants and derivatives of the MMP-8alt of SEQ ID NO:2, which fragments comprise at least amino acid 77 to amino acid 238 of SEQ ID NO:2.

In this regard a fragment is a polypeptide having an amino acid sequence that entirely is the same as part but not all of the amino acid sequence of the aforementioned MMP-8alt polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a MMP-8alt polypeptide of the present comprised within a precursor polypeptide designed for expression in a host and having heterologous pre and pro-polypeptide regions fused to the amino terminus of the MMP-8alt fragment and an additional region fused to the carboxyl terminus of the fragment. Therefore, fragments in one aspect of the meaning intended herein, refers to the portion or portions of a fusion polypeptide or fusion protein derived from MMP-8alt.

In this context about includes the particularly recited range and ranges larger or smaller by several, a few, 5, 4, 3, 2 or 1 amino acids at either extreme or at both extremes. Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions.

Further preferred regions are those that mediate activities of MMP-8alt. Most highly preferred in this regard are fragments that have a decreased chemical, biological or other activity of MMP-8alt.

Assays

The present invention relates to assays for diagnosing disease conditions by quantifying the level of expression of human MMP-8alt in a body tissue sample derived from a patient. Disease states include but are not limited to arthritis, and cancer, cancer metastases, and diseases caused by cellular apoptosis including but not limited to Parkinson's disease, Alzheimer's disease and Huntington's chorea. In accordance with a preferred embodiment of the invention there is provided a method of diagnosing disease conditions by quantifying human MMP-8alt mRNA expression in a body tissue sample derived from a patient. Examples of suitable body tissues include but are not limited to blood, serum, saliva, urine, synovial fluid, etc. In an aspect of the invention, the tissue sample is removed from a patient and reverse transcriptase-polymerase chain reaction (RT-PCR) is used to quantify the level of human MMP-8alt mRNA expression in the sample. The level of human MMP-8alt mRNA thus quantified is then compared to the level of human MMP-8alt mRNA expression from a host known not to have the disease condition in question and referred to herein as a "control". If the level of human MMP-8alt from the patient being diagnosed is substantially higher than that of the control this will indicate to the attending medical professional the onset of the disease. A substantially higher level of expression in this context refers to about three times or greater expression in the patient as compared to the control. In a preferred aspect of the invention the patient is a human and the human MMP-8alt is human MMP-8alt mRNA.

Other suitable exemplary methods for determining the level of expression of mRNA include Northern blot analysis, as described by, among others, J. Sambrook et al., Molecular Cloning, A Laboratory Manual (2d Ed. 1989) (Cold Spring Harbor Laboratory) which is hereby incorporated by reference in its entirety. A representative assay includes isolating total cellular RNA samples with RNAzol B system (Biotecx Laboratories, Inc., Houston, Tex. 77033). An acceptable quantity of total RNA is isolated from tissue samples. The RNA is size resolved by electrophoresis through a 1% agarose gel under strongly denaturing conditions. RNA is blotted from the gel onto a nylon filter, and the filter then is prepared for hybridization to a detectably labeled polynucleotide probe.

As a probe to detect mRNA that encodes human MMP-8alt, the antisense strand of the coding region of the human MMP8alt cDNA is labeled to a high specific activity. The cDNA is labeled by primer extension, using the Prime-It kit, available from Stratagene. The reaction is carried out using cDNA, following the standard reaction protocol as recommended by the supplier. The labeled polynucleotide is purified away from other labeled reaction components by column chromatography using a Select-G-50 column, obtained from 5-Prime - 3-Prime, Inc., Boulder, Colo. 80303.

The labeled probe is hybridized to the filter, at a concentration of 1,000,000 cpm/ml, in a small volume of 7% SDS, 0.5 M NaPO4, pH 7.4 at 65° C., overnight. Thereafter the probe solution is drained and the filter is washed twice at room temperature and twice at 60° C. with 0.5 x SSC, 0.1% SDS. The filter then is dried and exposed to film at −70° C. overnight with an intensifying screen. Autoradiography shows the level of human MMP-8alt mRNA.

The present invention also relates to diagnostic assays such as quantitative and diagnostic assays for detecting levels of human MMP-8alt polypeptide in cells and tissues, including determination of normal and abnormal levels. Thus, for instance, a diagnostic assay in accordance with the invention for detecting over-expression of human MMP-8alt polypeptide compared to normal control tissue samples may be used to detect the presence of arthritis, cancer, cancer metastases, and diseases caused by cellular apoptosis including but not limited to Parkinson's disease, Alzheimer's disease and Huntington's chorea. Assay techniques that can be used to determine levels of a polypeptide, such as a human MMP-8alt polypeptide of the present invention, in a sample derived from a host, are well-known to those of skill in the art. Such assay methods include radioimmunoassays, competitive-binding assays, Western Blot analysis and ELISA assays. Among these, ELISAs are preferred. An ELISA assay initially requires preparing an antibody specific to the antigen, human MMP-8alt, which can be monoclonal or polyconal. In addition a reporter antibody is prepared which binds to the specific antibody, or directly to the antigen itself. To the reporter antibody is attached a detectable entity such as a radioactive, fluorescent or enzymatic reagent, in this example horseradish peroxidase enzyme.

To carry out an ELISA the specific antibody to MMP-8alt is first incubated on a solid support, e.g. a polystyrene well, that binds the antibody permanently. Any free binding sites on the wells are then covered by incubating with an unrelated protein such as bovine serum albumin (hereinafter "BSA"). Next, sample removed from a host is incubated on the antibody bound to the wells; standards with known amounts of antigen may also be included to provide a quantitative measure. After the wells are washed with buffer, a second specific antibody to MMP-8alt, which either is a monoclonal or polyclonal antibody different from the first antibody used to coat the well, or is a specific antibody already conjugated to a detection reagent, is incubated in the wells. During this time the second antibody attaches to any human MMP-8alt polypeptides attached to the first antibody coated on the polystyrene well. Unbound antibody is washed out with buffer. If a reporter conjugated antibody has not already been used, a third antibody linked to a reporter molecule, e.g. horseradish peroxidase, is placed in the dish which can bind to the second antibody without binding to the first antibody used to coat the plate. Unattached reporter antibody is then washed out. A reagent to detect peroxidase activity, for example a colorimetric substrate, is then added to the well. Immobilized peroxidase, linked to human MMP-8alt polypeptide through the antibodies, produces a colored reaction product. The amount of color developed in a given time period indicates the amount of human MMP-8alt polypeptide present in the sample. Quantitative results typically are obtained by reference to a standard curve.

Also, antibodies may be used to quantify the amount of a protein present in a sample wherein antibodies specific to human MMP-8alt polypeptide are attached to a solid support and a sample derived from the host is passed over the solid support. The antibody is then eluted and the amount of bound MMP-8alt polypeptide is quantified. The amount of MMP-8alt polypeptide detected can be correlated to a quantity of human MMP-8alt polypeptide in the sample. The preferred body tissues employed for the above-described assays are synovial fluid, blood serum and urine with synovial fluid and serum being most preferred.

If the level of human MMP-8alt from the patient being diagnosed is substantially higher than that of the control this will indicate to the attending medical professional the onset of a disease condition. A substantially higher level of expression in this context refers to about three times or greater expression in the patient as compared to the control.

Vectors, Host Cells and Expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques.

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate transacting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skill, are set forth in great detail in Sambrook et al. cited elsewhere herein.

The DNA sequence in the expression vector may be operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region, a ribosome binding site for translation. The coding portion of the transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline, theomycin, kanamycin or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli,* Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Hosts for a great variety of expression constructs are well known, and those of skill will be enabled by the present disclosure readily to select a host for expressing a polypeptides in accordance with this aspect of the present invention.

Various mammalian cell culture systems can be employed for expression, as well. Examples of mammalian expression systems include the COS-7 lines of monkey kidney fibroblast, described in Gluzman et al., Cell 23: 175 (1981). Other cell lines capable of expressing a compatible vector include for example, the C 127, 3T3, CHO, HeLa, human kidney 293 and BHK cell lines.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among preferred eukaryotic vectors are pWLNEO, pSV2CAT, pOG44, pXT1 and pSG available from Stratagene; pcDNA3 available from Invitrogen; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("cat") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the *E. coli* lacI and lacZ promoters, the T3 and T7 promoters, the T5 tac promoter, the lambda PR, PL promoters and the trp promoter. Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host per se are routine skills in the art.

Generally, recombinant expression vectors will include origins of replication, a promoter derived from a highly-expressed gene to direct transcription of a downstream structural sequence, and a selectable marker to permit isolation of vector containing cells after exposure to the vector.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Constructs in host cells can be used in a conventional manner to produce the gene product encoded by the recombinant sequence. Alternatively, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, 2nd Ed., Cold Spring Harbor Laboratory Press, Cold Spring Harbor, N.Y. (1989).

The polypeptide may be expressed in a modified form, such as a fusion protein, and may include additional heterologous functional regions. Thus, for instance, a region of additional amino acids, particularly charged amino acids, may be added to the N-terminus of the polypeptide to improve stability and persistence in the host cell, during purification or during subsequent handling and storage. Also, regions may be added to the polypeptide to facilitate purification. Such regions may be removed prior to final preparation of the polypeptide. The addition of peptide moieties to polypeptides to engender excretion, to improve stability and to facilitate purification, among others, are familiar and routine techniques in the art.

Following transformation of a suitable host strain and growth of the host strain to an appropriate cell density, where the selected promoter is inducible it is induced by appropriate means (e.g., temperature shift or exposure to chemical inducer) and cells are cultured for an additional period. Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

The MMP-8alt polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography (HPLC) is employed for purification. Well known techniques for refolding protein may be employed to regenerate active conformation when the polypeptide is denatured during isolation and or purification.

MMP-8alt polynucleotides and polypeptides may be used in accordance with the present invention for a variety of applications, particularly the MMP-8alt polynucleotide and polypeptide may be used as a target to identify compounds which inhibit or retard expression of MMP-8alt polynucleotides or biological activity of MMP-8alt polypeptides to treat and/or prevent arthritis, cancer, cancer metastases, and diseases caused by cellular apoptosis including but not limited to Parkinson's disease, Alzheimer's disease and Huntington's chorea. Additional applications relate to diagnosis and to treatment of disorders of cells, tissues and organisms. These aspects of the invention are illustrated further by the following discussion.

Antibodies

The polypeptides, their fragments or other derivatives, or analogs thereof, or cells expressing them can be used as an immunogen to produce antibodies thereto as. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides or a fragment thereof into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide. The antibodies may also be used to bind a soluble form of the polypeptide and therefore render it ineffective to perform its intended biological function.

For preparation of monoclonal antibodies, any technique which provides antibodies produced by continuous cell line cultures can be used. Examples include the hybridoma technique (Kohler, G. and Milstein, C., Nature 256: 495–497 (1975), the a trioma technique, the human B-cell hybridoma technique (Kozbor et al., Immunology Today 4: 72 (1983) and the EBV-hybridoma technique to produce human monoclonal antibodies (Cole et al., pg. 77–96 in Monoclonal Antibodies and Cancer Therapy, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Antagonists

The invention also provides a method of identifying antagonists which reduce or block the action of human MMP-8alt protein, such as its interaction with human MMP-8alt-binding molecules or with MMP-8alt itself. For example, a cellular compartment, such as a membrane or a preparation thereof, such as a membrane-preparation, may be prepared from a cell that expresses a molecule that binds human MMP-8alt protein, such as a molecule of a signaling or regulatory pathway modulated by human MMP-8alt protein. The preparation is incubated with labeled human MMP-8alt protein in the absence or the presence of a candidate molecule which may be a human MMP-8alt antagonist. The ability of the candidate molecule to bind the binding molecule is reflected in decreased binding of the labeled ligand. Molecules which bind gratuitously, i.e., without inducing the effects of human MMP-8alt on binding the human MMP-8alt binding molecule, are most likely to be good antagonists.

Human MMP8alt-like effects of potential antagonists may by measured, for instance, by determining activity of a second messenger system following interaction of the candidate molecule with a cell or appropriate cell preparation, and comparing the effect with that of human MMP8alt or molecules that elicit the same effects as human MMP-8alt. Second messenger systems that may be useful in this regard include but are not limited to AMP guanylate cyclase, ion channel or phosphoinositide hydrolysis second messenger systems.

Another example of an assay for identifying human MMP-8alt antagonists is a competitive assay that combines human MMP8alt and a potential antagonist with an MMP-8alt substrate identified, for example, by the method as set forth in Example 3. Appropriate conditions for a competitive inhibition assay including optimal kinetic parameters are first determined with MMP8alt and an appropriate substrate. Human MMP-8alt activity is determined by measuring the disappearance of the substrate using HPLC. The same assay is then performed in the presence of a potential inhibitor or antagonist and the rate of disappearance of the substrate is again measured to determine the effectiveness of the candidate antagonist.

Potential antagonists include small organic molecules, peptides, polypeptides and antibodies which can pass through the cell membrane and bind to a polypeptide of the invention and thereby inhibit or extinguish its activity. Other potential antagonists include antisense molecules for preventing expression of the MMP-8alt gene. Antisense technology can be used to control gene expression through antisense DNA or RNA or through triple-helix formation. Antisense techniques are discussed, for example, in—Okano, J. Neurochem. 56: 560 (1991); Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene (or promotor) involved in transcription thereby preventing transcription and the production of human MMP-8alt. The antisense RNA oligonucleotide hybridizes to the mRNA in vivo and blocks translation of the mRNA molecule into human MMP-8alt polypeptide. The oligonucleotides described above can also be delivered to cells such that the antisense RNA or DNA may be expressed in vivo to inhibit production of human MMP-8alt.

The antagonists may be employed in a composition with a pharmaceutically acceptable carrier, e.g., as hereinafter described. The antagonists may be employed for instance to treat and/or prevent diseases or conditions including but not limited to arthritis, cancer and cancer metastases, diseases caused by cellular apoptosis including but not limited to Parkinson's disease, Alzheimer's disease and Huntington's chorea.

Compositions

The invention also relates to compositions comprising the antagonists. Thus, the antagonists of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of an antagonist of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to pharmaceutical packs and kits comprising one or more containers filled with one or more of the ingredients of the antagonists of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

The kits for performing the assay aspect of the invention include vials or vessels for incubating a body tissue sample, the components necessary for quantifying human MMP-8alt polynucleotides, for example, via RT-PCR. A kit for quantifying human MMP-8alt polypeptide may contain anti-MMP-8alt antibodies.

Administration

The antagonist compounds of the present invention may be administered as pharmaceutical compositions either alone or in conjunction with other compounds, such as therapeutic compounds.

The pharmaceutical compositions may be administered in any effective, convenient manner including, for instance, administration by topical, oral, anal, vaginal intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 $\mu$g/kg body weight. In most cases they will be administered in an amount not in excess of about 8 mg/kg body weight per day. Preferably, in most cases, dose is from about 10 $\mu$g/kg to about 1 mg/kg body weight, daily. It will be appreciated that optimum dosage will be determined by standard methods for each treatment modality and indication, taking into account the indication, its severity, route of administration, complicating conditions and the like.

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

EXAMPLES

All examples were carried out using standard techniques, which are well known and routine to those of skill in the art, except where otherwise described in detail. Routine molecular biology techniques of the following examples can be carried out as described in standard laboratory manuals, such as Sambrook et al., Molecular Cloning: A Laboratory Manual, 2nd Ed.; Cold Spring Harbor Laboratory Press, Cold Spring Harbor, N.Y. (1989).

Example 1 cDNA and genomic DNA cloning of MMP8alt

Cell culture

Two monocytic cell lines U937 and THP-1 cells were maintained in RPMI-1640 medium with 10% fetal bovine serum (Life Technologies, Inc.). Human chondrocytes were prepared from cartilage taken from patients undergoing joint replacement as described, Aydelotte M. B. and Kuettner K. E., (1988) Connect. Tissue Res. 18:205–222, and cultured in Dulbecco's modified medium with 10% fetal bovine serum.

cDNA and genomic DNA cloning

Total RNA isolation from THP-1 cells, U937 cells and human chondrocytes was accomplished using TriZol reagent (Life Technologies, Inc.). The RNA was reverse transcribed using the 1st Strand cDNA Synthesis Kit (Life Technologies, Inc.) and oligo-dT primer. PCR amplification of MMP-8 cDNA fragment corresponding to nucleotides 68 to 850 of the published sequence (GenBank Accession No. J05556) was performed with Pfu polymerase (Stratagene) for 30 cycles (95° C., 1 min; 55° C., 2 min; 72° C., 3 min) using primer pair AIB: A, sense: AATGG TACCG ATCAT GTTCT CCCTG AAGA (SEQ ID NO:5); B, antisense: ATGGC CTGAA TTCCA TCGAT GTCA (SEQ ID NO:6). A genomic DNA fragment containing the nucleotide sequence between 101 to 250 of the MMP-8 cDNA was generated by PCR with Taq polymerase (PE Applied Biosystems) for 30 cycles (95° C., 1 min; 54° C., 2 min; 72° C., 3 min with 3 sec extension after each cycle) using primer pair C/D: C, sense: GCTCT TACTC CATGT GCA (SEQ ID NO:7); D, antisense: ACGAT CACAT TAGTG CCA (SEQ ID NO:8). The relative position of the 91 bp exon generated by alternative splicing within the intron was determined by PCR using primer pair DlE: E, sense: CTACA GTAGT GAAGA GGA (SEQ ID NO:9). cDNAs containing the entire protein coding region of MMP-8 and MMP-8alt, were generated by RT-PCR and cloned into the Asp 718/Bam HI sites of pcDNA3+ vector (Invitrogen). DNA was sequenced using the dideoxy-mediated chain termination method of Sanger et al with a Sequenase 2.0 kit (United States Biochemical).

Example 2

Assay for In vitro translation and Autoactivation of MMP-8 and MMP-8alt

In vitro translation of MMP-8alt cDNA is subcloned into pCDNA3+ vector is accomplished using TNT T7 Coupled Reticulocyte Lysate System (Promega) with $^{35}$S-methionine (Amersham). In certain cases, canine pancreatic microsomal membranes (Promega) are also included in the in vitro translation reaction to detect co-translational processing and glycosylation. Samples of in vitro translated proteins 50 ml) are diluted to 1 ml with 50 mM Tris-HCl, pH 7.5, 0.2 mM NaCl, 10 mM $CaCl_2$, and 50 mM $ZnCl_2$, and concentrated with a Centricon 10 (Amicon) to a final volume of 50 ml. Samples are then diluted 10 fold with the same buffer containing 0.05% Brij-35 and are activated by treatment with 2 mM p-aminophenylmercuric acetate for 90 min at 37° C. In vito translated, $^{35}$S-labeled proteins are subjected to SDS-PAGE and autoradiography. The resultant sample sizes correspond to active MMP-8.

Example 3

Assay for identifying MMP-8alt Substrates and Antagonists

An expression cloning procedure is used to identify potential physiological substrates of MMP-8alt. Wen, L.-P. et al., (1997) J. Biol. Chem. 272, 26056–26061; Kothakota, S. et al., (1997) Science 278, 294–298. A chondrocyte cDNA library is prepared in the expression vector pBK-CMV (Statagene). This library is subdivided into small pools in which each pool represents 100 cDNA clones. These pools of cDNA are in vitro transcribed and translated in the presence of $^{35}$S-methionine (Amersham) using the TNT T3 Coupled Reticulocyte Lysate System (Promega). Each translated pool is separated into two parts; one portion is incubated with MMP-8alt, and the other portion is incubated with heat inactivated MMP-8alt. The reaction products are resolved by SDS-PAGE and visualized by autoradiography. Potential substrates are identified by comparing the pattern of $^{35}$S-labeled proteins in the samples treated with active and inactive MMP-8alt. Positive pools are then further subdivided and tested until individual cDNA clones are isolated. These isolated cDNA clones are sequenced to determine their identity. Potential substrates can then be tested in a whole cell setting by transfecting the cDNA into mammalian cells together with an MMP-8alt expression vector. A true substrate is expected to be cleaved by the MMP-8alt coexpressed in the cells at the same sites as the in vitro translated substrate.

Once the substrates are identified, they may be used directly as substrates for screening potential antagonists of MMP-8alt. In addition, the cleavage sites in these potential substrates are identified by amino acid sequencing, and synthetic substrates are designed based on the amino acid sequence of the cleavage sites.

Although the present invention has been described in considerable detail with reference to certain preferred versions thereof, other versions are possible without departing from the spirit and scope of the preferred versions contained herein.

All references referred to herein are hereby incorporated by reference in their entirety.

SEQUENCE LISTING

```
<160> NUMBER OF SEQ ID NOS: 9

<210> SEQ ID NO 1
<211> LENGTH: 2314
<212> TYPE: DNA
<213> ORGANISM: Homo sapiens
<220> FEATURE:
<221> NAME/KEY: CDS
<222> LOCATION: (232)..(1566)

<400> SEQUENCE: 1

gctcgccagg gaagggccct acccagagga cagaaagaaa gccaggaggg gtagagtttg     60
```

-continued

```
aagagaagat catgttctcc ctgaagacgc ttccatttct gctcttactc catgtgcaga    120

tttccaaggc ctttcctgta tcttctaaag agaaaaatac aaaaactgtt cagcagaata    180

aataagcctt ttctacagta gtgaagagga taaaaaagag gaactgcact g atg caa     237
                                                         Met Gln
                                                           1

caa ata cct caa gag aag tca att aat gac tac ctg gaa aag ttc tac      285
Gln Ile Pro Gln Glu Lys Ser Ile Asn Asp Tyr Leu Glu Lys Phe Tyr
          5                  10                  15

caa tta cca agc aac cag tat cag tct aca agg aag aat ggc act aat      333
Gln Leu Pro Ser Asn Gln Tyr Gln Ser Thr Arg Lys Asn Gly Thr Asn
     20                  25                  30

gtg atc gtt gaa aag ctt aaa gaa atg cag cga ttt ttt ggg ttg aat      381
Val Ile Val Glu Lys Leu Lys Glu Met Gln Arg Phe Phe Gly Leu Asn
 35                  40                  45                  50

gtg acg ggg aag cca aat gag gaa act ctg gac atg atg aaa aag cct      429
Val Thr Gly Lys Pro Asn Glu Glu Thr Leu Asp Met Met Lys Lys Pro
                 55                  60                  65

cgc tgt gga gtg cct gac agt ggt ggt ttt atg tta acc cca gga aac      477
Arg Cys Gly Val Pro Asp Ser Gly Gly Phe Met Leu Thr Pro Gly Asn
             70                  75                  80

ccc aag tgg gaa cgc act aac ttg acc tac agg att cga aac tat acc      525
Pro Lys Trp Glu Arg Thr Asn Leu Thr Tyr Arg Ile Arg Asn Tyr Thr
         85                  90                  95

cca cag ctg tca gag gct gag gta gaa aga gct atc aag gat gcc ttt      573
Pro Gln Leu Ser Glu Ala Glu Val Glu Arg Ala Ile Lys Asp Ala Phe
    100                 105                 110

gaa ctc tgg agt gtt gca tca cct ctc atc ttc acc agg atc tca cag      621
Glu Leu Trp Ser Val Ala Ser Pro Leu Ile Phe Thr Arg Ile Ser Gln
115                 120                 125                 130

gga gag gca gat atc aac att gct ttt tac caa aga gat cac ggt gac      669
Gly Glu Ala Asp Ile Asn Ile Ala Phe Tyr Gln Arg Asp His Gly Asp
                135                 140                 145

aat tct cca ttt gat gga ccc aat gga atc ctt gct cat gcc ttt cag      717
Asn Ser Pro Phe Asp Gly Pro Asn Gly Ile Leu Ala His Ala Phe Gln
            150                 155                 160

cca ggc caa ggt att gga gga gat gct cat ttt gat gcc gaa gaa aca      765
Pro Gly Gln Gly Ile Gly Gly Asp Ala His Phe Asp Ala Glu Glu Thr
        165                 170                 175

tgg acc aac acc tcc gca aat tac aac ttg ttt ctt gtt gct gct cat      813
Trp Thr Asn Thr Ser Ala Asn Tyr Asn Leu Phe Leu Val Ala Ala His
    180                 185                 190

gaa ttt ggc cat tct ttg ggg ctc gct cac tcc tct gac cct ggt gcc      861
Glu Phe Gly His Ser Leu Gly Leu Ala His Ser Ser Asp Pro Gly Ala
195                 200                 205                 210

ttg atg tat ccc aac tat gct ttc agg gaa acc agc aac tac tca ctc      909
Leu Met Tyr Pro Asn Tyr Ala Phe Arg Glu Thr Ser Asn Tyr Ser Leu
                215                 220                 225

cct caa gat gac atc gat ggc att cag gcc atc tat gga ctt tca agc      957
Pro Gln Asp Asp Ile Asp Gly Ile Gln Ala Ile Tyr Gly Leu Ser Ser
            230                 235                 240

aac cct atc caa cct act gga cca agc aca ccc aaa ccc tgt gac ccc     1005
Asn Pro Ile Gln Pro Thr Gly Pro Ser Thr Pro Lys Pro Cys Asp Pro
        245                 250                 255

agt ttg aca ttt gat gct atc acc aca ctc cgt gga gaa ata ctt ttc     1053
Ser Leu Thr Phe Asp Ala Ile Thr Thr Leu Arg Gly Glu Ile Leu Phe
    260                 265                 270

ttt aaa gac agg tac ttc tgg aga agg cat cct cag cta caa aga gtc     1101
Phe Lys Asp Arg Tyr Phe Trp Arg Arg His Pro Gln Leu Gln Arg Val
275                 280                 285                 290
```

-continued

```
gaa atg aat ttt att tct cta ttc tgg cca tcc ctt cca act ggt ata     1149
Glu Met Asn Phe Ile Ser Leu Phe Trp Pro Ser Leu Pro Thr Gly Ile
                295                 300                 305

cag gct gct tat gaa gat ttt gac aga gac ctc att ttc cta ttt aaa     1197
Gln Ala Ala Tyr Glu Asp Phe Asp Arg Asp Leu Ile Phe Leu Phe Lys
            310                 315                 320

ggc aac caa tac tgg gct ctg agt ggc tat gat att ctg caa ggt tat     1245
Gly Asn Gln Tyr Trp Ala Leu Ser Gly Tyr Asp Ile Leu Gln Gly Tyr
        325                 330                 335

ccc aag gat ata tca aac tat ggc ttc ccc agc agc gtc caa gca att     1293
Pro Lys Asp Ile Ser Asn Tyr Gly Phe Pro Ser Ser Val Gln Ala Ile
    340                 345                 350

gac gca gct gtt ttc tac aga agt aaa aca tac ttc ttt gta aat gac     1341
Asp Ala Ala Val Phe Tyr Arg Ser Lys Thr Tyr Phe Phe Val Asn Asp
355                 360                 365                 370

caa ttc tgg aga tat gat aac caa aga caa ttc atg gag cca ggt tat     1389
Gln Phe Trp Arg Tyr Asp Asn Gln Arg Gln Phe Met Glu Pro Gly Tyr
                375                 380                 385

ccc aaa agc ata tca ggt gcc ttt cca gga ata gag agt aaa gtt gat     1437
Pro Lys Ser Ile Ser Gly Ala Phe Pro Gly Ile Glu Ser Lys Val Asp
            390                 395                 400

gca gtt ttc cag caa gaa cat ttc ttc cat gtc ttc agt gga cca aga     1485
Ala Val Phe Gln Gln Glu His Phe Phe His Val Phe Ser Gly Pro Arg
        405                 410                 415

tat tac gca ttt gat ctt att gct cag aga gtt acc aga gtt gca aga     1533
Tyr Tyr Ala Phe Asp Leu Ile Ala Gln Arg Val Thr Arg Val Ala Arg
    420                 425                 430

ggc aat aaa tgg ctt aac tgt aga tat ggc tga agcaaaatca aatgtggctg   1586
Gly Asn Lys Trp Leu Asn Cys Arg Tyr Gly
435                 440                 445

tatccacttt cagaatgttg aagggaagtt cagcatgcat tttcgttaca ttgtgtcctg   1646

cttatacttt tctcaatatt aagtcattgt ttcccatcac tgtatccatt ctacctgtcc   1706

tccgtgaaaa tatgtttgga atattccact atttgcagag gcttattcag ttcttacaca   1766

ttccatctta cattagtgat tccatcaaag agaaggaaag taagcctttt tgtcacctca   1826

atatttacta tttcaatact tacatatctg acttctagga tttattgtta tattacttgc   1886

ctatctgact tcatacatcc ctcagtttct taaaatgtcc tatgtatatc ttctacatgc   1946

aatttagaac tagattttgg ttagaagtaa ggattataaa caacctagac agtacccttg   2006

gcctttacag aaaatatggt gctgttttct acccttggaa agaaatgtag atgatatgtt   2066

tcgtgggttg aattgtgtcc cccataaaag atatgttgaa gttctaaccc caggtaccca   2126

tgaatgtgag cttaccaggg tctttgcaga tgtaattagt taagttaagg tgagatcaca   2186

ctgaattagg gtgggctcta aatccattat gactgttgtt cttataagaa gaagagagca   2246

tagccaccta ggggaggagg ccgtgtgaag acagaggcag agattggagt gacgcatctc   2306

caagccaa                                                            2314
```

<210> SEQ ID NO 2
<211> LENGTH: 444
<212> TYPE: PRT
<213> ORGANISM: Homo sapiens

<400> SEQUENCE: 2

```
Met Gln Gln Ile Pro Gln Glu Lys Ser Ile Asn Asp Tyr Leu Glu Lys
  1               5                  10                  15

Phe Tyr Gln Leu Pro Ser Asn Gln Tyr Gln Ser Thr Arg Lys Asn Gly
```

-continued

```
            20                  25                  30

Thr Asn Val Ile Val Glu Lys Leu Lys Glu Met Gln Arg Phe Phe Gly
        35                  40                  45

Leu Asn Val Thr Gly Lys Pro Asn Glu Glu Thr Leu Asp Met Met Lys
    50                  55                  60

Lys Pro Arg Cys Gly Val Pro Asp Ser Gly Gly Phe Met Leu Thr Pro
65                  70                  75                  80

Gly Asn Pro Lys Trp Glu Arg Thr Asn Leu Thr Tyr Arg Ile Arg Asn
                85                  90                  95

Tyr Thr Pro Gln Leu Ser Glu Ala Glu Val Glu Arg Ala Ile Lys Asp
            100                 105                 110

Ala Phe Glu Leu Trp Ser Val Ala Ser Pro Leu Ile Phe Thr Arg Ile
        115                 120                 125

Ser Gln Gly Glu Ala Asp Ile Asn Ile Ala Phe Tyr Gln Arg Asp His
    130                 135                 140

Gly Asp Asn Ser Pro Phe Asp Gly Pro Asn Gly Ile Leu Ala His Ala
145                 150                 155                 160

Phe Gln Pro Gly Gln Gly Ile Gly Gly Asp Ala His Phe Asp Ala Glu
                165                 170                 175

Glu Thr Trp Thr Asn Thr Ser Ala Asn Tyr Asn Leu Phe Leu Val Ala
            180                 185                 190

Ala His Glu Phe Gly His Ser Leu Gly Leu Ala His Ser Ser Asp Pro
        195                 200                 205

Gly Ala Leu Met Tyr Pro Asn Tyr Ala Phe Arg Glu Thr Ser Asn Tyr
    210                 215                 220

Ser Leu Pro Gln Asp Asp Ile Asp Gly Ile Gln Ala Ile Tyr Gly Leu
225                 230                 235                 240

Ser Ser Asn Pro Ile Gln Pro Thr Gly Pro Ser Thr Pro Lys Pro Cys
                245                 250                 255

Asp Pro Ser Leu Thr Phe Asp Ala Ile Thr Thr Leu Arg Gly Glu Ile
            260                 265                 270

Leu Phe Phe Lys Asp Arg Tyr Phe Trp Arg Arg His Pro Gln Leu Gln
        275                 280                 285

Arg Val Glu Met Asn Phe Ile Ser Leu Phe Trp Pro Ser Leu Pro Thr
    290                 295                 300

Gly Ile Gln Ala Ala Tyr Glu Asp Phe Asp Arg Asp Leu Ile Phe Leu
305                 310                 315                 320

Phe Lys Gly Asn Gln Tyr Trp Ala Leu Ser Gly Tyr Asp Ile Leu Gln
                325                 330                 335

Gly Tyr Pro Lys Asp Ile Ser Asn Tyr Gly Phe Pro Ser Ser Val Gln
            340                 345                 350

Ala Ile Asp Ala Ala Val Phe Tyr Arg Ser Lys Thr Tyr Phe Phe Val
        355                 360                 365

Asn Asp Gln Phe Trp Arg Tyr Asp Asn Gln Arg Gln Phe Met Glu Pro
    370                 375                 380

Gly Tyr Pro Lys Ser Ile Ser Gly Ala Phe Pro Gly Ile Glu Ser Lys
385                 390                 395                 400

Val Asp Ala Val Phe Gln Gln Glu His Phe Phe His Val Phe Ser Gly
                405                 410                 415

Pro Arg Tyr Tyr Ala Phe Asp Leu Ile Ala Gln Arg Val Thr Arg Val
            420                 425                 430

Ala Arg Gly Asn Lys Trp Leu Asn Cys Arg Tyr Gly
        435                 440
```

-continued

<210> SEQ ID NO 3
<211> LENGTH: 2223
<212> TYPE: DNA
<213> ORGANISM: Homo sapiens
<220> FEATURE:
<221> NAME/KEY: CDS
<222> LOCATION: (72)..(1475)

<400> SEQUENCE: 3

```
gctcgccagg gaagggccct acccagagga cagaaagaaa gccaggaggg gtagagtttg     60

aagagaagat c atg ttc tcc ctg aag acg ctt cca ttt ctg ctc tta ctc     110
             Met Phe Ser Leu Lys Thr Leu Pro Phe Leu Leu Leu Leu
               1               5                  10

cat gtg cag att tcc aag gcc ttt cct gta tct tct aaa gag aaa aat      158
His Val Gln Ile Ser Lys Ala Phe Pro Val Ser Ser Lys Glu Lys Asn
     15                  20                  25

aca aaa act gtt cag gac tac ctg gaa aag ttc tac caa tta cca agc      206
Thr Lys Thr Val Gln Asp Tyr Leu Glu Lys Phe Tyr Gln Leu Pro Ser
 30                  35                  40                  45

aac cag tat cag tct aca agg aag aat ggc act aat gtg atc gtt gaa      254
Asn Gln Tyr Gln Ser Thr Arg Lys Asn Gly Thr Asn Val Ile Val Glu
                 50                  55                  60

aag ctt aaa gaa atg cag cga ttt ttt ggg ttg aat gtg acg ggg aag      302
Lys Leu Lys Glu Met Gln Arg Phe Phe Gly Leu Asn Val Thr Gly Lys
             65                  70                  75

cca aat gag gaa act ctg gac atg atg aaa aag cct cgc tgt gga gtg      350
Pro Asn Glu Glu Thr Leu Asp Met Met Lys Lys Pro Arg Cys Gly Val
         80                  85                  90

cct gac agt ggt ggt ttt atg tta acc cca gga aac ccc aag tgg gaa      398
Pro Asp Ser Gly Gly Phe Met Leu Thr Pro Gly Asn Pro Lys Trp Glu
     95                 100                 105

cgc act aac ttg acc tac agg att cga aac tat acc cca cag ctg tca      446
Arg Thr Asn Leu Thr Tyr Arg Ile Arg Asn Tyr Thr Pro Gln Leu Ser
110                 115                 120                 125

gag gct gag gta gaa aga gct atc aag gat gcc ttt gaa ctc tgg agt      494
Glu Ala Glu Val Glu Arg Ala Ile Lys Asp Ala Phe Glu Leu Trp Ser
                130                 135                 140

gtt gca tca cct ctc atc ttc acc agg atc tca cag gga gag gca gat      542
Val Ala Ser Pro Leu Ile Phe Thr Arg Ile Ser Gln Gly Glu Ala Asp
            145                 150                 155

atc aac att gct ttt tac caa aga gat cac ggt gac aat tct cca ttt      590
Ile Asn Ile Ala Phe Tyr Gln Arg Asp His Gly Asp Asn Ser Pro Phe
        160                 165                 170

gat gga ccc aat gga atc ctt gct cat gcc ttt cag cca ggc caa ggt      638
Asp Gly Pro Asn Gly Ile Leu Ala His Ala Phe Gln Pro Gly Gln Gly
    175                 180                 185

att gga gga gat gct cat ttt gat gcc gaa gaa aca tgg acc aac acc      686
Ile Gly Gly Asp Ala His Phe Asp Ala Glu Glu Thr Trp Thr Asn Thr
190                 195                 200                 205

tcc gca aat tac aac ttg ttt ctt gtt gct gct cat gaa ttt ggc cat      734
Ser Ala Asn Tyr Asn Leu Phe Leu Val Ala Ala His Glu Phe Gly His
                210                 215                 220

tct ttg ggg ctc gct cac tcc tct gac cct ggt gcc ttg atg tat ccc      782
Ser Leu Gly Leu Ala His Ser Ser Asp Pro Gly Ala Leu Met Tyr Pro
            225                 230                 235

aac tat gct ttc agg gaa acc agc aac tac tca ctc cct caa gat gac      830
Asn Tyr Ala Phe Arg Glu Thr Ser Asn Tyr Ser Leu Pro Gln Asp Asp
        240                 245                 250

atc gat ggc att cag gcc atc tat gga ctt tca agc aac cct atc caa      878
```

-continued

```
Ile Asp Gly Ile Gln Ala Ile Tyr Gly Leu Ser Ser Asn Pro Ile Gln
    255                 260                 265

cct act gga cca agc aca ccc aaa ccc tgt gac ccc agt ttg aca ttt      926
Pro Thr Gly Pro Ser Thr Pro Lys Pro Cys Asp Pro Ser Leu Thr Phe
270                 275                 280                 285

gat gct atc acc aca ctc cgt gga gaa ata ctt ttc ttt aaa gac agg      974
Asp Ala Ile Thr Thr Leu Arg Gly Glu Ile Leu Phe Phe Lys Asp Arg
                290                 295                 300

tac ttc tgg aga agg cat cct cag cta caa aga gtc gaa atg aat ttt     1022
Tyr Phe Trp Arg Arg His Pro Gln Leu Gln Arg Val Glu Met Asn Phe
            305                 310                 315

att tct cta ttc tgg cca tcc ctt cca act ggt ata cag gct gct tat     1070
Ile Ser Leu Phe Trp Pro Ser Leu Pro Thr Gly Ile Gln Ala Ala Tyr
        320                 325                 330

gaa gat ttt gac aga gac ctc att ttc cta ttt aaa ggc aac caa tac     1118
Glu Asp Phe Asp Arg Asp Leu Ile Phe Leu Phe Lys Gly Asn Gln Tyr
    335                 340                 345

tgg gct ctg agt ggc tat gat att ctg caa ggt tat ccc aag gat ata     1166
Trp Ala Leu Ser Gly Tyr Asp Ile Leu Gln Gly Tyr Pro Lys Asp Ile
350                 355                 360                 365

tca aac tat ggc ttc ccc agc agc gtc caa gca att gac gca gct gtt     1214
Ser Asn Tyr Gly Phe Pro Ser Ser Val Gln Ala Ile Asp Ala Ala Val
                370                 375                 380

ttc tac aga agt aaa aca tac ttc ttt gta aat gac caa ttc tgg aga     1262
Phe Tyr Arg Ser Lys Thr Tyr Phe Phe Val Asn Asp Gln Phe Trp Arg
            385                 390                 395

tat gat aac caa aga caa ttc atg gag cca ggt tat ccc aaa agc ata     1310
Tyr Asp Asn Gln Arg Gln Phe Met Glu Pro Gly Tyr Pro Lys Ser Ile
        400                 405                 410

tca ggt gcc ttt cca gga ata gag agt aaa gtt gat gca gtt ttc cag     1358
Ser Gly Ala Phe Pro Gly Ile Glu Ser Lys Val Asp Ala Val Phe Gln
    415                 420                 425

caa gaa cat ttc ttc cat gtc ttc agt gga cca aga tat tac gca ttt     1406
Gln Glu His Phe Phe His Val Phe Ser Gly Pro Arg Tyr Tyr Ala Phe
430                 435                 440                 445

gat ctt att gct cag aga gtt acc aga gtt gca aga ggc aat aaa tgg     1454
Asp Leu Ile Ala Gln Arg Val Thr Arg Val Ala Arg Gly Asn Lys Trp
                450                 455                 460

ctt aac tgt aga tat ggc tga agcaaaatca aatgtggctg tatccacttt        1505
Leu Asn Cys Arg Tyr Gly
            465

cagaatgttg aagggaagtt cagcatgcat tttcgttaca ttgtgtcctg cttatacttt   1565

tctcaatatt aagtcattgt ttcccatcac tgtatccatt ctacctgtcc tccgtgaaaa   1625

tatgtttgga atattccact atttgcagag gcttattcag ttcttacaca ttccatctta   1685

cattagtgat tccatcaaag agaaggaaag taagcctttt tgtcacctca atatttacta   1745

tttcaatact tacatatctg acttctagga tttattgtta tattacttgc ctatctgact   1805

tcatacatcc ctcagtttct taaaatgtcc tatgtatatc ttctacatgc aatttagaac   1865

tagattttgg ttagaagtaa ggattataaa caacctagac agtacccttg gcctttacag   1925

aaaatatggt gctgttttct acccttggaa agaaatgtag atgatatgtt tcgtgggttg   1985

aattgtgtcc cccataaaag atatgttgaa gttctaaccc caggtaccca tgaatgtgag   2045

cttaccaggg tctttgcaga tgtaattagt taagttaagg tgagatcaca ctgaattagg   2105

gtgggctcta aatccattat gactgttgtt cttataagaa gaagagagca tagccaccta   2165

ggggaggagg ccgtgtgaag acagaggcag agattggagt gacgcatctc caagccaa     2223
```

-continued

<210> SEQ ID NO 4
<211> LENGTH: 467
<212> TYPE: PRT
<213> ORGANISM: Homo sapiens

<400> SEQUENCE: 4

Met Phe Ser Leu Lys Thr Leu Pro Phe Leu Leu Leu Leu His Val Gln
1 5 10 15

Ile Ser Lys Ala Phe Pro Val Ser Ser Lys Glu Lys Asn Thr Lys Thr
20 25 30

Val Gln Asp Tyr Leu Glu Lys Phe Tyr Gln Leu Pro Ser Asn Gln Tyr
35 40 45

Gln Ser Thr Arg Lys Asn Gly Thr Asn Val Ile Val Glu Lys Leu Lys
50 55 60

Glu Met Gln Arg Phe Phe Gly Leu Asn Val Thr Gly Lys Pro Asn Glu
65 70 75 80

Glu Thr Leu Asp Met Met Lys Lys Pro Arg Cys Gly Val Pro Asp Ser
85 90 95

Gly Gly Phe Met Leu Thr Pro Gly Asn Pro Lys Trp Glu Arg Thr Asn
100 105 110

Leu Thr Tyr Arg Ile Arg Asn Tyr Thr Pro Gln Leu Ser Glu Ala Glu
115 120 125

Val Glu Arg Ala Ile Lys Asp Ala Phe Glu Leu Trp Ser Val Ala Ser
130 135 140

Pro Leu Ile Phe Thr Arg Ile Ser Gln Gly Glu Ala Asp Ile Asn Ile
145 150 155 160

Ala Phe Tyr Gln Arg Asp His Gly Asp Asn Ser Pro Phe Asp Gly Pro
165 170 175

Asn Gly Ile Leu Ala His Ala Phe Gln Pro Gly Gln Gly Ile Gly Gly
180 185 190

Asp Ala His Phe Asp Ala Glu Glu Thr Trp Thr Asn Thr Ser Ala Asn
195 200 205

Tyr Asn Leu Phe Leu Val Ala Ala His Glu Phe Gly His Ser Leu Gly
210 215 220

Leu Ala His Ser Ser Asp Pro Gly Ala Leu Met Tyr Pro Asn Tyr Ala
225 230 235 240

Phe Arg Glu Thr Ser Asn Tyr Ser Leu Pro Gln Asp Asp Ile Asp Gly
245 250 255

Ile Gln Ala Ile Tyr Gly Leu Ser Ser Asn Pro Ile Gln Pro Thr Gly
260 265 270

Pro Ser Thr Pro Lys Pro Cys Asp Pro Ser Leu Thr Phe Asp Ala Ile
275 280 285

Thr Thr Leu Arg Gly Glu Ile Leu Phe Phe Lys Asp Arg Tyr Phe Trp
290 295 300

Arg Arg His Pro Gln Leu Gln Arg Val Glu Met Asn Phe Ile Ser Leu
305 310 315 320

Phe Trp Pro Ser Leu Pro Thr Gly Ile Gln Ala Ala Tyr Glu Asp Phe
325 330 335

Asp Arg Asp Leu Ile Phe Leu Phe Lys Gly Asn Gln Tyr Trp Ala Leu
340 345 350

Ser Gly Tyr Asp Ile Leu Gln Gly Tyr Pro Lys Asp Ile Ser Asn Tyr
355 360 365

Gly Phe Pro Ser Ser Val Gln Ala Ile Asp Ala Ala Val Phe Tyr Arg
370 375 380

```
Ser Lys Thr Tyr Phe Phe Val Asn Asp Gln Phe Trp Arg Tyr Asp Asn
385                 390                 395                 400

Gln Arg Gln Phe Met Glu Pro Gly Tyr Pro Lys Ser Ile Ser Gly Ala
                405                 410                 415

Phe Pro Gly Ile Glu Ser Lys Val Asp Ala Val Phe Gln Gln Glu His
            420                 425                 430

Phe Phe His Val Phe Ser Gly Pro Arg Tyr Tyr Ala Phe Asp Leu Ile
        435                 440                 445

Ala Gln Arg Val Thr Arg Val Ala Arg Gly Asn Lys Trp Leu Asn Cys
    450                 455                 460

Arg Tyr Gly
465


<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide sense primer

<400> SEQUENCE: 5

aatggtaccg atcatgttct ccctgaaga                                        29


<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide antisense primer

<400> SEQUENCE: 6

atggcctgaa ttccatcgat gtca                                             24


<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide sense primer

<400> SEQUENCE: 7

gctcttactc catgtgca                                                    18


<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide antisense primer

<400> SEQUENCE: 8

acgatcacat tagtgcca                                                    18


<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide sense primer
```

-continued

<400> SEQUENCE: 9 ctacagtagt gaagagga 18

What is claimed is:

1. An isolated polynucleotide comprising a member selected from the group consisting of:

(a) a polynucleotide having at least 90% identity to a polynucleotide encoding a polypeptide comprising an amino acid sequence as set forth in SEQ ID NO:2; and (b) a polynucleotide which is complementary to the polynucleotide of (a).

2. The polynucleotide of claim 1 wherein the polynucleotide is DNA.

3. The polynucleotide of claim 2 which encodes the polypeptide comprising an amino acid sequence as set forth in SEQ ID NO:2.

4. The polynucleotide of claim 2 which encodes the polypeptide comprising amino acid 77 to amino acid 238 of SEQ ID NO:2.

5. The polynucleotide of claim 1 wherein the polynucleotide is RNA.

6. The polynucleotide of claim 1 wherein the polynucleotide is genomic DNA.

7. The polynucleotide of claim 1 comprising the sequence as set forth in SEQ ID NO:1.

8. An isolated polynucleotide having at least 95% identity to a polynucleotide comprising nucleotide 174 to nucleotide 2314 of SEQ ID NO:2.

9. An isolated polypeptide comprising an amino acid sequence which is at least 90% identical to the amino acid sequence set forth in SEQ ID NO:2.

10. The polypeptide of claim 9 wherein the polypeptide comprises amino acid 77 to amino acid 238 of SEQ ID NO:2.

11. The polypeptide of claim 9 comprising the amino acid sequence of SEQ ID NO:2.

12. A process for producing a human MMP-8alt polypeptide comprising:

(a) transforming a host cell with a vector comprising DNA which upon expression encodes the polypeptide of claim 9;

(b) culturing the host cell under conditions promoting expression of the polypeptide; and (c) recovering the expressed polypeptide.

13. A human MMP-8alt polypeptide prepared by the process of claim 12.

14. A process for producing a cell which expresses a polypeptide comprising transforming the cell with a vector comprising DNA which upon expression encodes the polypeptide of claim 9.

15. A cell prepared by the process of claim 14.

16. A host cell transformed with a vector comprising DNA which upon expression encodes the polypeptide of claim 9.

17. An antibody which binds to the polypeptide of claim 9.

18. A method of producing an antibody comprising: injecting MMP-8alt into a mammal;

purifying the antibody produced by the mammal; and recovering the antibody.

19. A method for diagnosing the presence and/or progression of a disease state in a mammal comprising:

(a) isolating an MMP-8alt polynucleotide from a body tissue sample derived from the mammal;

(b) quantifying the level of expression of the MMP-8alt polynucleotide; and (c) comparing the level of expression determined in step (b) to a control to detect the presence or absence of an over-expression of the polynucleotide.

20. The method of claim 19 wherein the body tissue sample is selected from the group consisting of, urine, blood and synovial fluid.

21. The method of claim 19 wherein the disease state is selected from the group consisting of arthritis, cancer, Parkinson's disease, Alzheimer's disease and Huntington's chorea.

22. The method of claim 19 wherein the polynucleotide is mRNA and the level of mRNA is quantified via RT-PCR.

23. A method for diagnosing the presence and/or progression of a disease state in a mammal comprising:

(a) isolating an MMP-8alt polypeptide from a body tissue sample derived from the mammal;

(b) quantifying the amount of MMP-8alt polypeptide in the sample; and (c) comparing the amount determined in step (b) to a control to determine the presence or absence of an elevated quantity of the polypeptide.

24. The method of claim 23 wherein the body tissue sample is selected from the group consisting of urine, blood and synovial fluid.

25. The method of claim 23 wherein the disease state is selected from the group consisting of arthritis, cancer, Parkinson's disease, Alzheimer's disease and Huntington's chorea.

26. A method for identifying substances that antagonize or prevent the activity of MMP-8alt protein comprising:

(a) contacting MMP-8alt protein with a substance; and (b) determining the ability of the substance to antagonize or prevent the activity of MMP-8alt protein as compared to a control.

27. The method of claim 26 wherein the MMP-8alt protein and substance are combined with a substrate of the MMP-8alt protein under conditions sufficient for the MMP-8alt protein to act on the substrate and the ability of the substance to prevent MMP-8alt from acting on the substrate is determined by quantifying the amount of substrate cleaved by MMP-8alt protein.

28. A substance identified by the method of claim 26.

29. A method for treating a disease associated with an over-expression of MMP-8alt protein comprising administering a therapeutically effective amount of the substance of claim 28 to a subject in need thereof.

30. A pharmaceutical composition comprising the substance of claim 28 and a pharmaceutically acceptable carrier.

31. A diagnostic kit for detecting a disease state associated with an over-expression of MMP-8alt protein comprising an anti-human MMP-8alt antibody;

A diagnostic kit for detecting disease states associated with an over-expression of human MMP-8alt mRNA.

* * * * *